United States Patent [19]
Walters

[11] Patent Number: 5,916,244
[45] Date of Patent: Jun. 29, 1999

[54] EXTERNAL HEART STIMULATION ELECTRODE HAVING REDUCED EDGE EFFECT

[75] Inventor: Warren R. Walters, Lakeville, Minn.

[73] Assignee: Katecho, Inc., Des Moines, Iowa

[21] Appl. No.: 09/017,191

[22] Filed: Feb. 20, 1998

[51] Int. Cl.[6] ........................................... A61N 1/04
[52] U.S. Cl. ............................................... 607/142
[58] Field of Search ..................................... 607/142

[56] References Cited

U.S. PATENT DOCUMENTS

| | | |
|---|---|---|
| 4,419,998 | 12/1983 | Heath . |
| 4,848,345 | 7/1989 | Zenkich . |
| 5,063,932 | 11/1991 | Dahl et al. . |
| 5,111,812 | 5/1992 | Swanson et al. . |
| 5,295,482 | 3/1994 | Clare et al. . |
| 5,356,428 | 10/1994 | Way . |
| 5,520,683 | 5/1996 | Subramaniam et al. . |
| 5,571,165 | 11/1996 | Ferrari . |

*Primary Examiner*—William E. Kamm
*Assistant Examiner*—Carl H. Layno
*Attorney, Agent, or Firm*—Zarley, McKee, Thomte, Voorhees & Sease

[57] ABSTRACT

An external electrode for stimulating a person's heart is comprised of a first conductive layer having a first perimetric edge. A second conductive layer is in electrical contact with the first conductive layer and includes a protruding portion extending at least partially outwardly beyond the first perimetric edge of the first conductive layer. A third conductive layer is in electrical contact with both of the first conductive layer and the protruding portion of the second conductive layer. An electrical lead is connected to the first conductive layer.

16 Claims, 5 Drawing Sheets

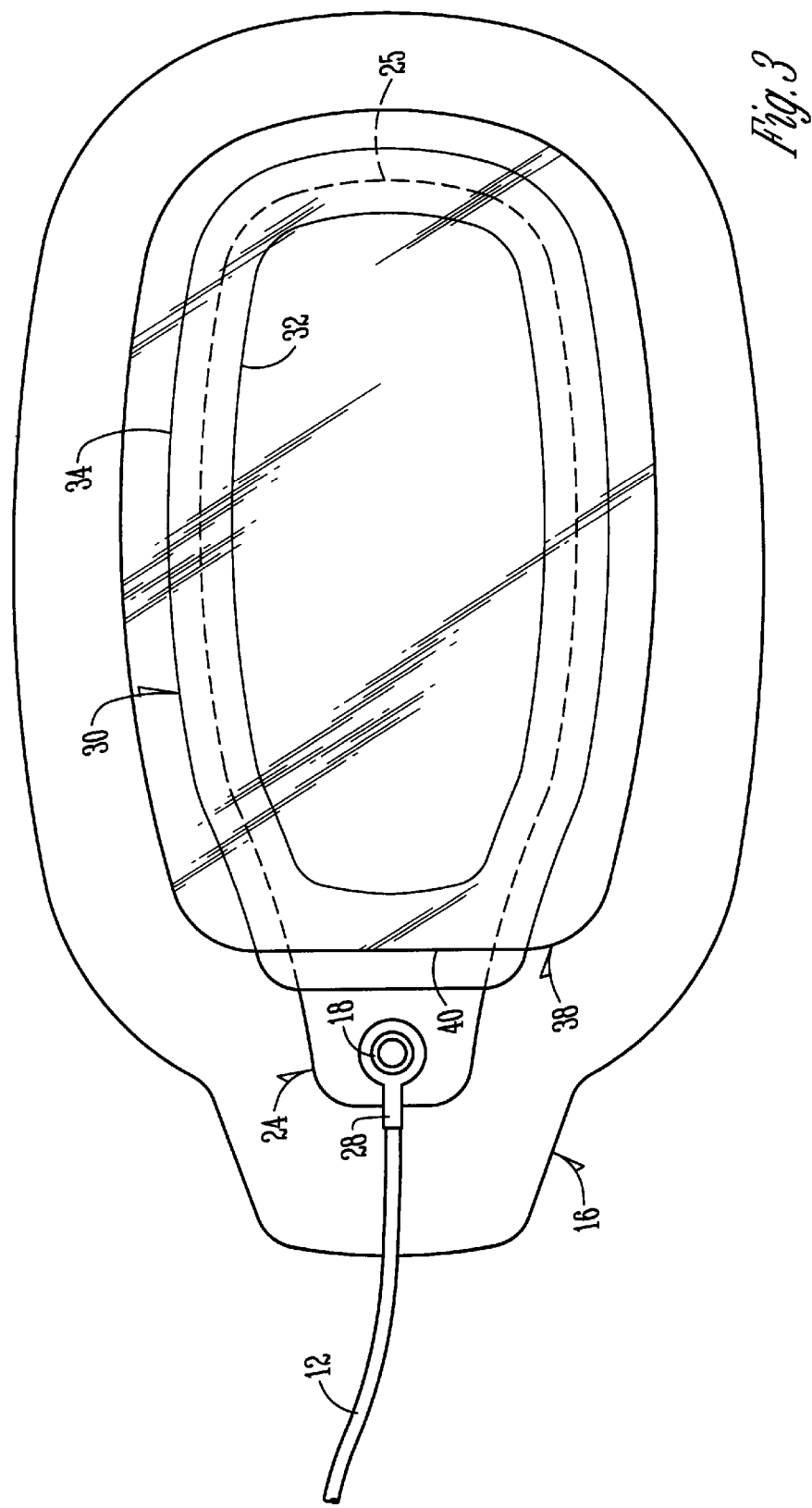

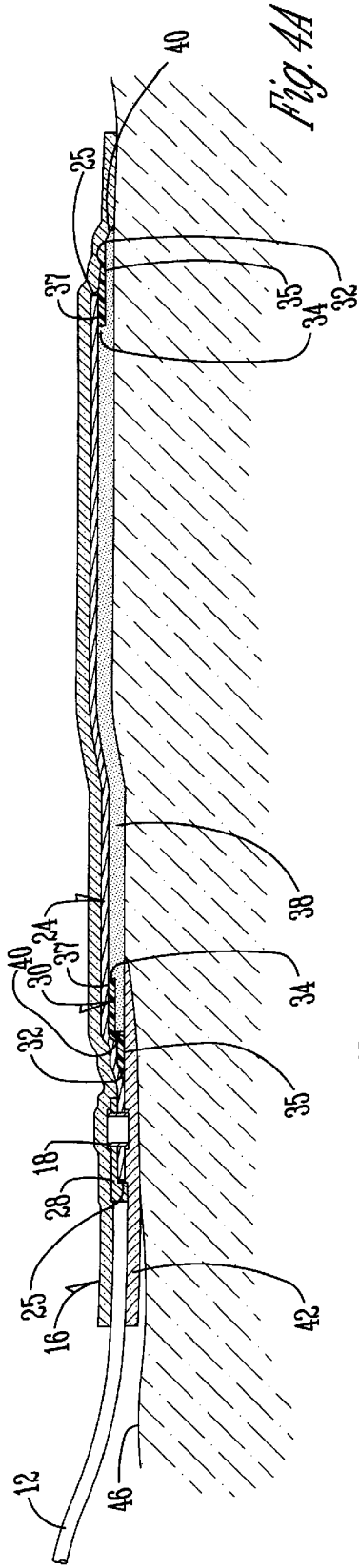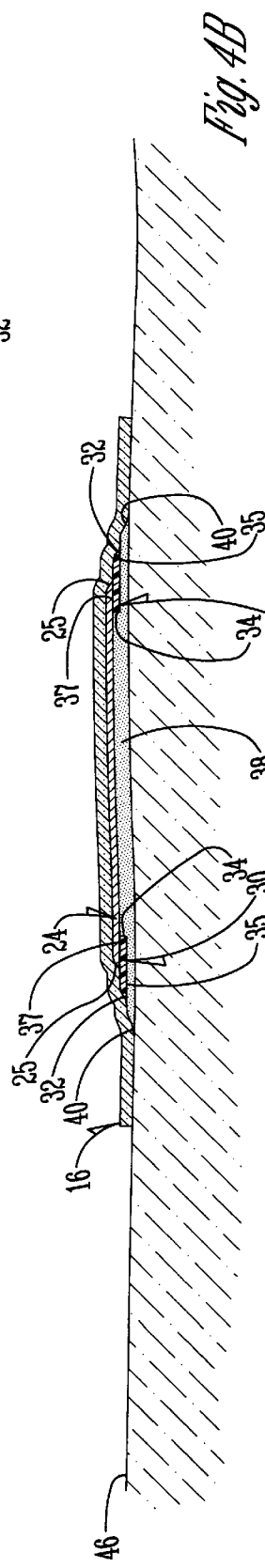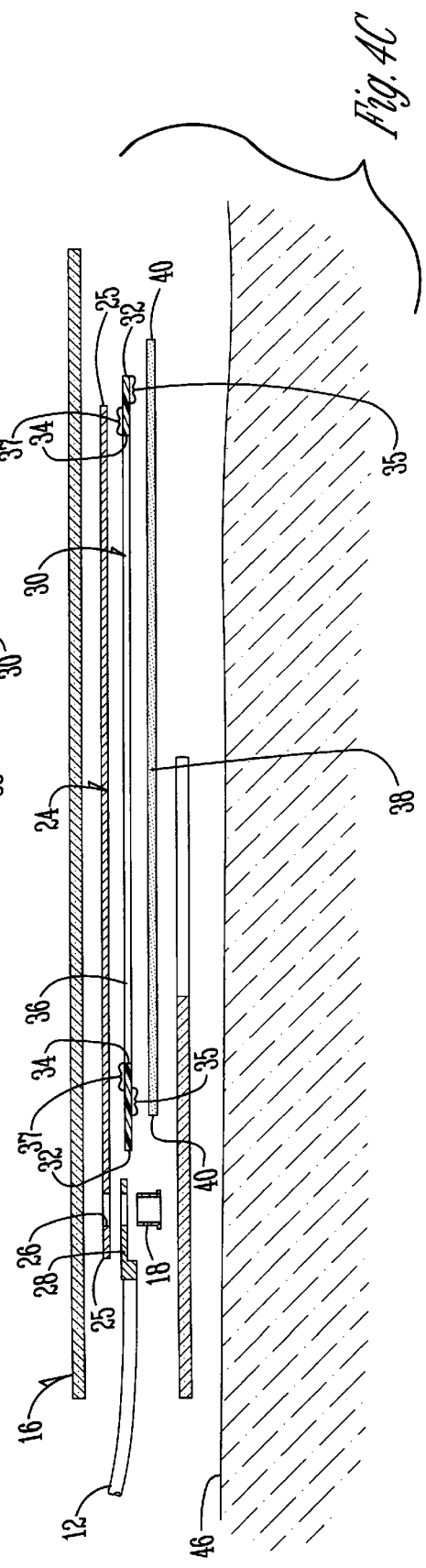

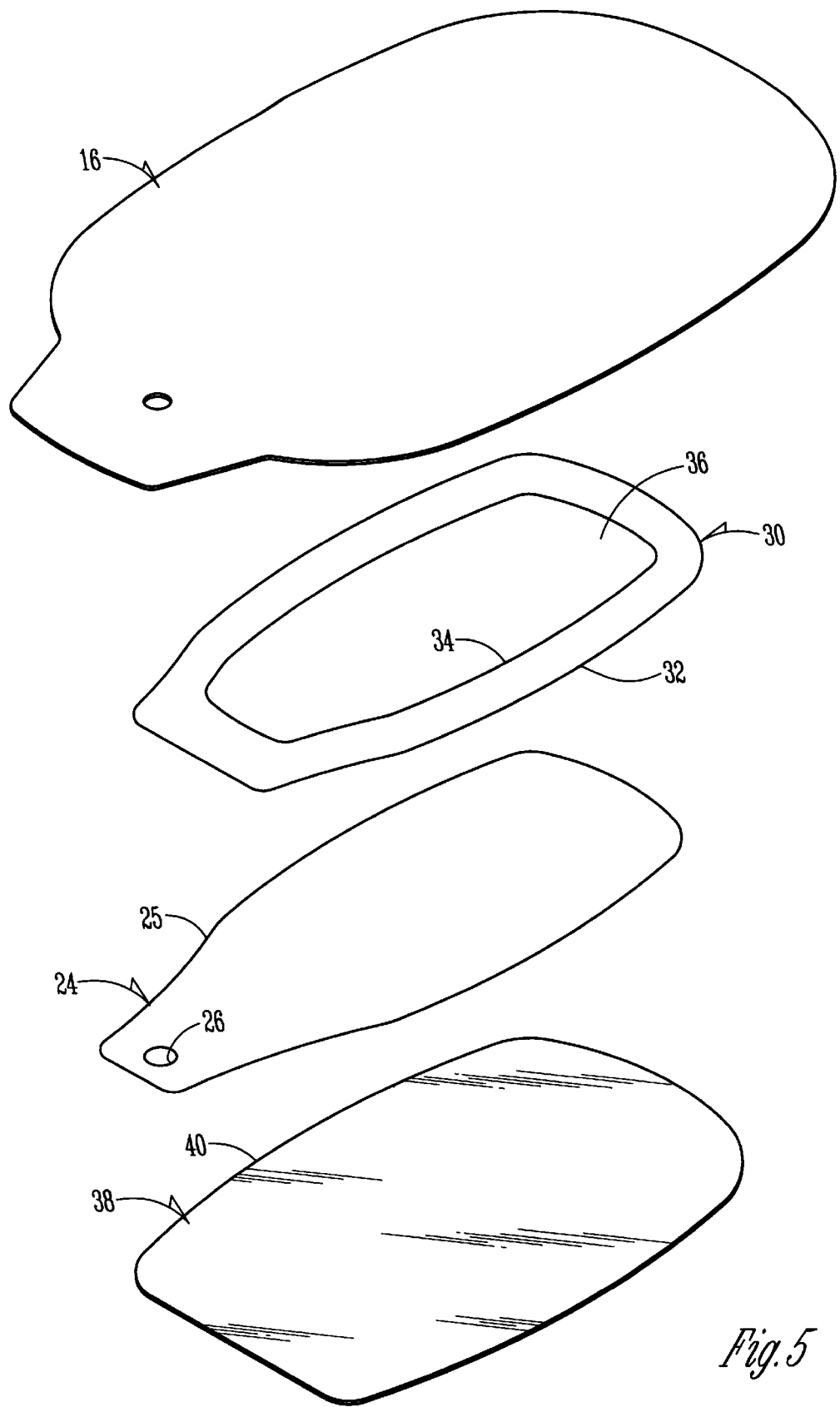

EXTERNAL HEART STIMULATION ELECTRODE HAVING REDUCED EDGE EFFECT

BACKGROUND OF THE INVENTION

The present invention relates to external heart stimulation electrodes, and more particularly relates to an external heart stimulation electrode which has a reduced "edge effect".

External heart stimulation electrodes are used for such functions as defibrillation, external pacing, and monitoring of a patient's heart. The electrodes are placed on the external skin of the patient and include lead wires which connect to a console for controlling the particular function of the electrode. The console is capable of using the electrode as a monitoring electrode for monitoring electrical impulses generated by the heartbeat, and for registering those impulses on a screen for monitoring by a paramedic or physician.

The console may also be used for introducing a high charge of electricity to the electrode which shocks the patient's heart during a time when the patient's heart is fibrillating. The monitor can also be used to introduce a periodic electrical impulse to the electrode which stimulates the heart in periodic intervals, thereby causing a pacing of the heartbeat.

One problem encountered with current electrodes, particularly during the defibrillating or pacing function, is commonly referred to as "edge effect". Edge effect results when the charge induced on the electrode intensifies at the outer edges of the electrode rather than being spread uniformly throughout the entire surface of the electrode. This intensification adjacent the edge of the electrode sometimes results in burning of the patient.

Therefore a primary object of the present invention is the provision of an improved external heart stimulation electrode having a reduced edge effect.

A further object of the present invention is the provision of an improved external heart stimulation electrode having a reduced edge effect, and being simple in construction and efficient in operation.

SUMMARY OF THE INVENTION

The forgoing objects are achieved by an external electrode for stimulating a persons heart comprising first, second, and third conductive layers. The first conductive layer has a first perimetric edge. The second conductive layer is in electrical contact with the first conductive layer and has an exposed portion extending at least partially outwardly beyond the first perimetric edge of the first conductive layer. The third conductive layer is in electrical conduct with both of the first conductive layer and the exposed portion of the second conductive layer. An electrical lead is connected to the first conductive layer.

In one modification of the present invention the second conductive layer is between the first and third conductive layers. In a second embodiment of the present invention the first conductive layer is positioned between the second and third conductive layers.

The first conductive layer can be metal or other highly conductive material, and is preferably constructed of tin or tin coated material. Other metals may be used such as silver. Another example of material for the first conductive layer is a carbon loaded vinyl having a silver or silver chloride layer on the outer surface thereof.

The second conductive layer is preferably a carbon loaded vinyl material capable of conducting electricity. However, any electrically conductive material may be used so long as it has a conductivity less than the first conductive layer.

The third conductive layer can be formed of a conductive medium commonly referred to as a hydrogel. Various types of hydrogel may be used, including, but not limited to a hydrogel manufactured by LecTech Corporation in Minneapolis, Minn. under the product name LT3300. Another example of a hydrogel is a hydrogel manufactured by Ludlow Technical Products, 2 Ludlow Park, Chicopee, Mass. 01022, under the product designation RG63B or RG63T. Numerous other suitable conductive mediums may be utilized, including liquid chemistry gels such as a gel manufactured by Parker Laboratories, 307-T Washington Street, Orange, N.J. 07050 under the product designation EK 214-08.91.

BRIEF DESCRIPTION OF THE FIGURES OF THE DRAWINGS

FIG. 3 is a plan view of one of the electrodes shown in FIG. 1.

FIG. 4A is a sectional view taken along line 4A—4A of FIG. 1.

FIG. 4B is a sectional view taken along line 4B—4B of FIG. 1.

FIG. 4C is an exploded view of the various layers shown in FIG. 4A.

FIG. 5 is an exploded view similar to that shown in FIG. 2, but showing a modified arrangement of the various layers.

DETAILED DESCRIPTION OF THE PREFERRED EMBODIMENT

Figure 1:
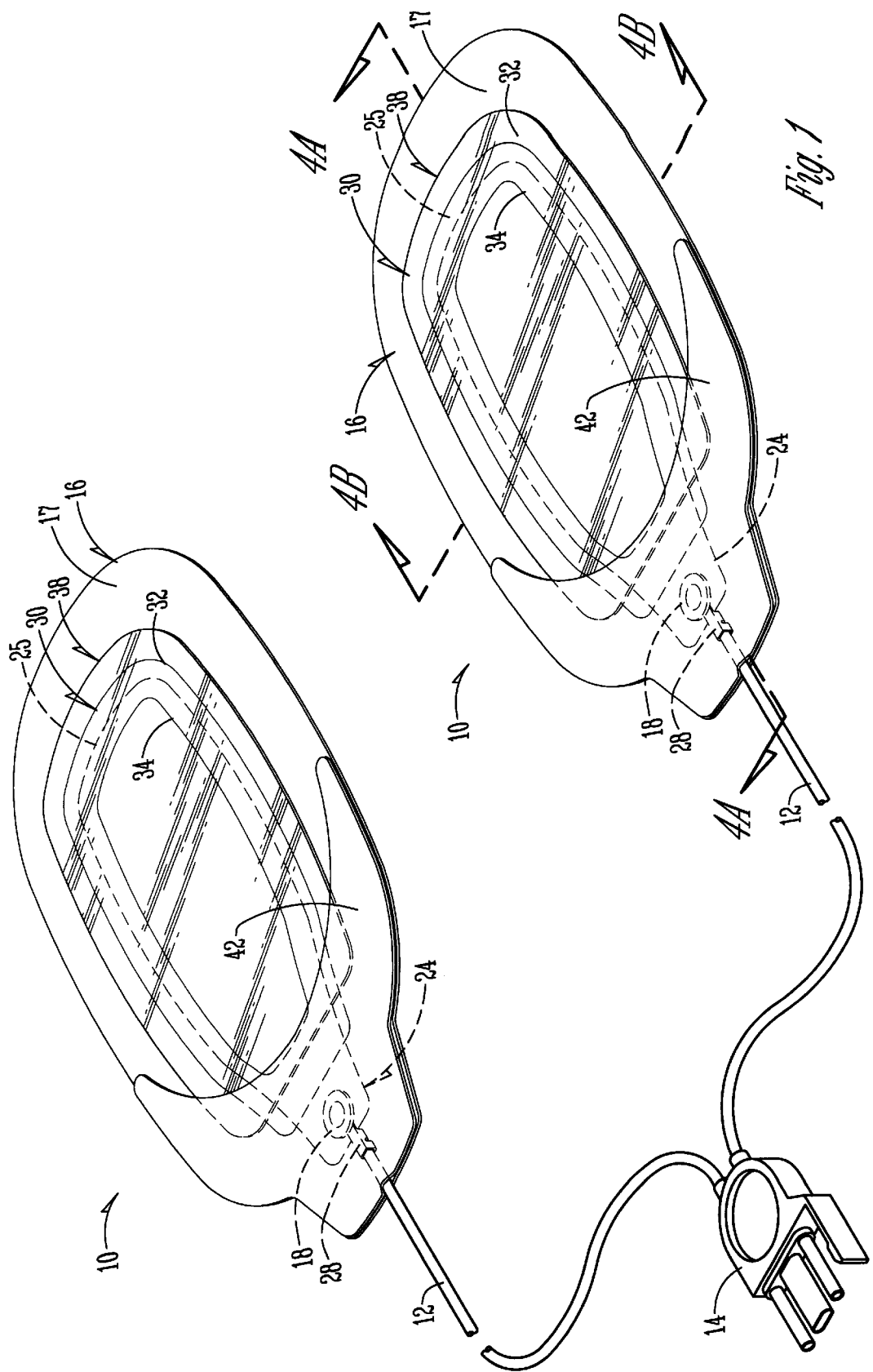
FIG. 1 is a perspective view of a pair of electrodes of the present invention, having the release liners removed from the electrodes, and being connected by a single connector.

Referring to FIG. 1, a pair of external heart stimulation electrodes of the present invention are designated by the numeral 10. Each of the electrodes 10 includes a lead wire 12 which extends into a connecting plug 14. Connecting plug 14 is adapted to be plugged into the wires (not shown) of a monitoring/pacing/defibrillation console commonly sold by many manufacturers in the industry.

Figure 2:
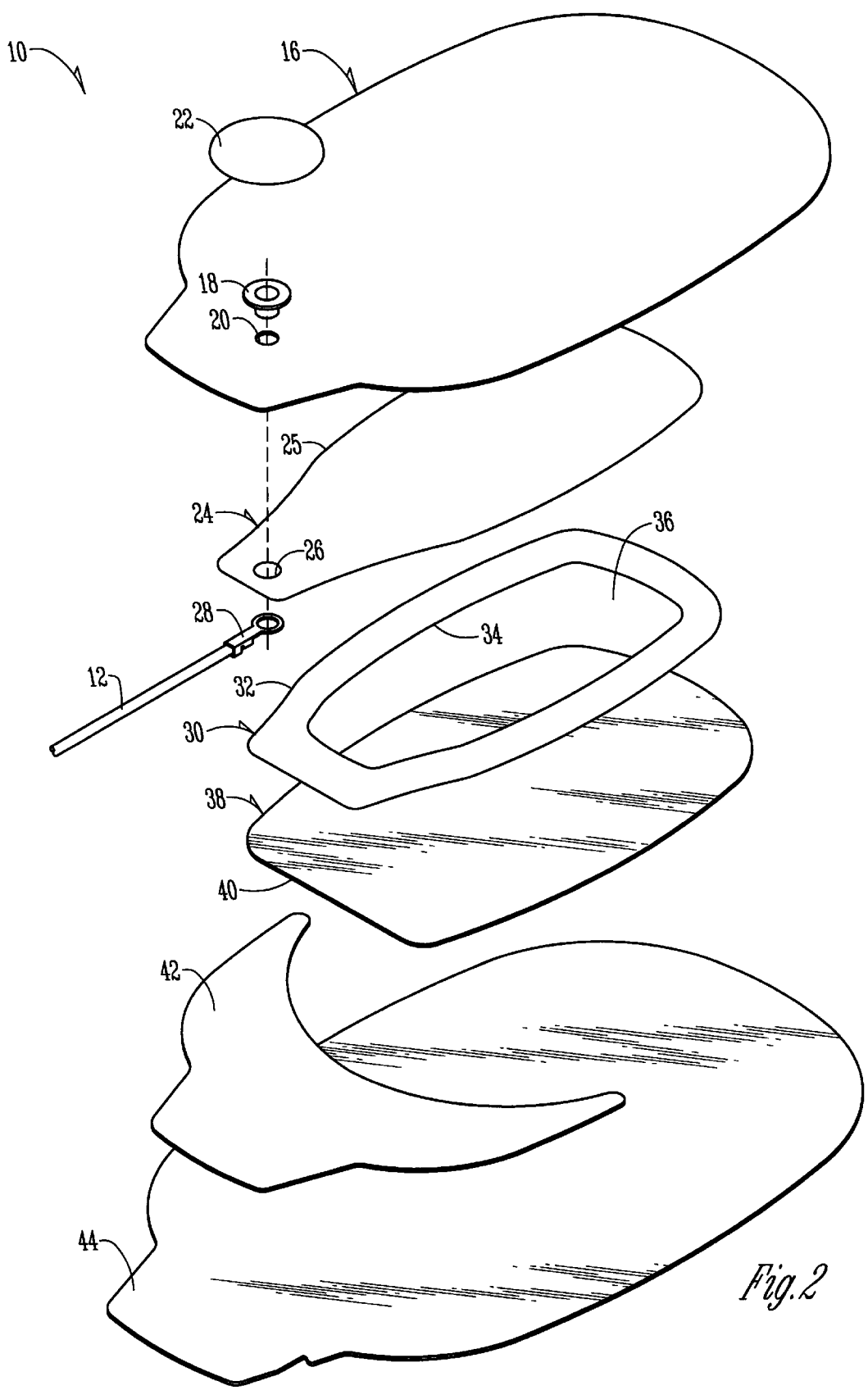
FIG. 2 is an exploded view of the various components of the electrode of the present invention.

FIG. 2 shows the various components of each of the electrodes 10 of FIG. 1. The layers are shown in top to bottom reverse order from that which appears in FIG. 1. A dielectric backing sheet 16 is comprised of a plastic material which does not conduct electricity. The lower surface (as viewed in FIG. 2) of sheet 16 is shown in FIG. 1 to have an adhesive film 17 extending around its outer perimeter for engagement and adherence to the outer skin of a patient during use of the electrode.

A rivet 18 extends through a rivet hole 20 in sheet 16 and is adapted to be covered by a circular dielectric pad 22 so as to prevent accidental electrical contact between the user of the electrode and the rivet 18.

Below dielectric sheet 16 is a conductive sheet 24 which is preferably comprised of tin. However, other good electrical conductors could be used instead of tin including other metals, and including, but not limited to, plastic or PVC sheet material covered with metal films such as tin, silver, or silver chloride. The primary requirement for the material of sheet 24 is that it be highly conductive. Sheet 24 includes a rivet hole 26 in to which rivet 18 is fitted, and includes an outer primeter 25.

Below tin sheet 24 is a connecting grommet 28 into which rivet 18 is fitted and attached to connect the grommet 28 with the tin sheet 24 and provide good electrical contact therebetween. Connecting grommet 28 is connected to lead 12 which in turn is connected to the connector 14 and the console (not shown) so as to permit the console to direct various electrical impulses to the sheet 24.

Below tin sheet 24 is a frame sheet 30 having an outer perimeter 32 and an inner perimeter 34 which defines an opening 36 therein. As can best be seen in FIG. 4B, the frame sheet 30 is positioned with the outer perimeter 25 of the tin sheet 24 in such a manner that the outer perimeter 25 of the tin sheet 24 is located between and spaced from the inner perimeter 34 and the outer perimeter 32 of frame sheet 30. This causes a protruding edge 35 of frame sheet 30 to protrude outwardly beyond the outer perimeter 25 of the tin sheet 24. Similarly the frame sheet 30 includes an inner edge surface 37 which is in contact with the downwardly presented surface of tin sheet 24 adjacent the perimeter thereof.

Positioned below the frame sheet 30 is a hydrogel sheet 38 which is comprised of a conductive medium including an electrolyte dissolved within a polymer scrim material. Such hydrogels are commonly used for external heart stimulation electrodes. Some electrodes may use liquid gels without the scrim material, but the hydrogels are preferred. Hydrogel sheet 38 includes an outer perimeter 40 which extends outwardly beyond the outer edges 32 of the frame sheet 30 as can be seen in FIGS. 4A and 4B.

Positioned below the transparent hydrogel 38 is a crescent shaped end cover 42 formed of dielectric material. End cover 42 covers the left end (as viewed in FIGS. 1 and 2) of the electrodes.

Referring again to FIG. 2, a transparent release liner 44 is placed in covering relation over the end cover 42 and the remainder of the electrode. The release liner 44 protects the hydrogel sheet 38 which, while also being a good electrical conductor, includes an adhesive material therein and is very tacky.

During use the release liner 44 is removed so that the electrodes appear as shown in FIG. 1, 4A, and 4B. The electrode is placed against the skin 46 of the patient with the hydrogel layer 38 in contact with the patient's skin 46. The hydrogel is tacky and adheres to the patient's skin and forms a good electrical contact therewith.

Once in place the electrodes can be used to monitor the heart by receiving electrical impulses generated by the heartbeat of the patient. These electrical impulses pass through the conductive medium, and into the tin material by virtue of the contact between the hydrogel layer 38 and the tin layer 34. The impulses are then conducted back through lead wires 12 to the console where electrical circuitry analyzes the impulses.

The electrodes can be used to defibrillate a patient who has gone into fibrillation by causing the console to introduce a high charge of electricity to the foil sheet 24. The foil sheet 24, particularly when it is formed of a very good electrical conductor such as metal, does not distribute the charge evenly across its entire surface. Instead the charge tends to accumulate adjacent the edge of the tin or other metal sheet 24. This charge which accumulates adjacent the edges 25 of the sheet 24 passes into the inner edge surface 37 of the frame sheet 30 and is conducted laterally outwardly therefrom to the protruding edge 35 of the frame sheet 30. The charge accumulated adjacent the edge 25 of the metal sheet 24 is thus spread to a wider area, and is ultimately conducted into the hydrogel 38.

The end result is that the higher charge which accumulates the edges 25 of the conductive sheet 24 is spread out before it passes into the conductive hydrogel 38, thereby decreasing its intensity and minimizing the tendency to burn the patient's skin 46 during fibrillation. The hydrogel 38 is in close adhesive and electrical contact with the foil sheet 24 through the window or opening 36 as can be seen in FIGS. 4A and 4B. The result is a more even distribution of the charge across the entire surface of the hydrogel 40.

In relative size, the foil sheet 24 is smaller than the outer perimeter 32 of the frame sheet 30, and is larger than the inner perimeter 34 of the frame sheet 30. Similarly the outer perimeter 32 of the frame sheet 30 is smaller than the outer perimeter 40 of the hydrogel 38.

Referring to FIG. 5, a modified form of the invention is shown. The electrode of FIG. 5 is constructed of the same components as the electrode of FIG. 2, with the exception that the metal sheet 24 is positioned between the frame sheet 30 and the hydrogel sheet 44. In this arrangement, the frame sheet 30 spreads the electrical charge adjacent the top surface of foil sheet 24 and distributes it downwardly onto the hydrogel 34. While it is possible to place the foil sheet 24 between the frame sheet 30 and the hydrogel 44 as shown in FIG. 5, the preferred embodiment is the arrangement shown in FIG. 2 with the frame sheet 30 positioned between the foil sheet 24 and the hydrogel 38.

The sheet members 24, 30, and 38 in the present invention may have properties of electrical conductivity that are the same relative to one another, or which vary in any possible combination relative to one another. However, it is preferred that the electrical conductivity of sheet member 30 be less than the electrical conductivity of sheet member 24.

In the drawings and specification there has been set forth a preferred embodiment of the invention, and although specific terms are employed, these are used in a generic and descriptive sense only and not for purposes of limitation. Changes in the form and the proportion of parts as well as in the substitution of equivalents are contemplated as circumstances may suggest or render expedient without departing from the spirit or scope of the invention as further defined in the following claims.

What is claimed is:

1. An external electrode for stimulating a person's heart comprising:
    a first conductive layer having a first perimetric edge;
    a second conductive layer in electrical contact with said first conductive layer and having a protruding portion extending at least partially outwardly beyond said first perimetric edge of said first conductive layer;
    a third conductive layer in electrical contact with both of said first conductive layer and said protruding portion of said second conductive layer; and
    an electrical lead connected to said first conductive layer.

2. An external electrode according to claim 1 having an arrangement wherein said second conductive layer is between said first and third conductive layers.

3. An external electrode according to claim 1 having an arrangement wherein said first conductive layer is between said second and third conductive layers.

4. An external electrode according to claim 1 wherein said first conductive layer comprises a metal.

5. An external electrode according to claim 4 wherein said first conductive layer comprises tin.

6. An external electrode according to claim 5 wherein said third conductive layer comprises a hydrogel.

7. An external electrode according to claim 6 wherein said second conductive layer is comprised of less conductive material than said first conductive layer.

8. An external electrode according to claim 7 wherein said second conductive layer is comprised of carbon-loaded polyvinyl chloride.

9. An external electrode according to claim 1 wherein said second conductive layer includes a central opening therein having an opening edge located inwardly from said first perimetric edge of said first conductive layer.

10. An electrode for stimulating a heart externally comprising:

a first conductive layer having a first perimetric edge, and upper and lower surfaces;

an electrical lead connected to said first conductive layer for delivering an electrical current thereto;

a second conductive layer;

a third conductive layer having upper and lower surfaces; said lower surface of said first conductive layer being in electrical contact with said upper surface of said third conductive layer;

said second conductive layer being in electrical contact with said first conductive layer adjacent at least a portion of said first perimetric edge thereof;

said second conductive layer being in electrical contact with said third conductive layer for conducting electrical current from the area adjacent said first perimetric edge of said first conductive layer to said third conductive layer.

11. An electrode according to claim 10 wherein said first conductive layer is comprised at least partially of metal.

12. An electrode according to claim 10 having an arrangement wherein said second conductive layer contacts said lower surface of said first conductive layer and said upper surface of said third conductive layer.

13. An electrode according to claim 10 having an arrangement wherein said second conductive layer contacts said upper surface of said first conductive layer and said upper surface of said third conductive layer.

14. An electrode according to claim 10 wherein said second conductive layer includes an opening therein.

15. An electrode according to claim 14 wherein said second conductive layer includes a border at least partially surrounding said opening.

16. An electrode according to claim 15 having an arrangement wherein said first conductive layer contacts said third conductive layer through said opening in said second conductive layer.

\* \* \* \* \*